US012064389B2

(12) United States Patent
Spector

(10) Patent No.: US 12,064,389 B2
(45) Date of Patent: Aug. 20, 2024

(54) METHOD FOR IMPROVING KIDNEY FUNCTION WITH EXTRACORPOREAL SHOCKWAVES

(71) Applicant: Avner Spector, Savyon (IL)

(72) Inventor: Avner Spector, Savyon (IL)

( * ) Notice: Subject to any disclaimer, the term of this patent is extended or adjusted under 35 U.S.C. 154(b) by 0 days.

(21) Appl. No.: 18/051,990

(22) Filed: Nov. 2, 2022

(65) Prior Publication Data

US 2023/0285226 A1 Sep. 14, 2023

Related U.S. Application Data

(63) Continuation of application No. 16/776,901, filed on Jan. 30, 2020, now Pat. No. 11,517,499, which is a continuation of application No. 15/452,568, filed on Mar. 7, 2017, now Pat. No. 10,583,069, which is a continuation of application No. 13/359,538, filed on Jan. 27, 2012, now abandoned.

(51) Int. Cl.
| | |
|---|---|
| *A61H 23/00* | (2006.01) |
| *A61B 17/22* | (2006.01) |
| *A61B 17/225* | (2006.01) |
| *A61H 23/02* | (2006.01) |
| *A61N 7/02* | (2006.01) |
| *A61B 18/00* | (2006.01) |

(52) U.S. Cl.
CPC ......... *A61H 23/008* (2013.01); *A61B 17/225* (2013.01); *A61B 17/2251* (2013.01); *A61H 23/02* (2013.01); *A61N 7/02* (2013.01); *A61B 2018/00404* (2013.01); *A61B 2018/00434* (2013.01); *A61B 2018/00511* (2013.01)

(58) Field of Classification Search
CPC .................. A61H 23/00; A61H 23/008; A61H 2205/087; A61B 17/22004; A61B 8/085; A61B 8/13; A61B 2090/378
See application file for complete search history.

(56) References Cited

U.S. PATENT DOCUMENTS

| | | | | |
|---|---|---|---|---|
| 6,390,995 | B1 * | 5/2002 | Ogden | A61B 17/2256 601/2 |
| 7,507,213 | B2 * | 3/2009 | Schultheiss | A61H 23/008 601/4 |
| 7,985,189 | B1 * | 7/2011 | Ogden | A61H 23/008 601/2 |
| 2006/0036194 | A1 * | 2/2006 | Schultheiss | A61H 23/008 601/2 |
| 2006/0036195 | A1 * | 2/2006 | Schultheiss | A61H 23/008 601/2 |
| 2006/0100552 | A1 * | 5/2006 | Schultheiss | A61H 23/008 601/2 |
| 2006/0246044 | A1 * | 11/2006 | Lutz | A61P 9/00 601/1 |

(Continued)

*Primary Examiner* — Tu A Vo
(74) *Attorney, Agent, or Firm* — Shalom Wertsberger; Saltamar Innovations

(57) ABSTRACT

A method for treating a kidney with focused extracorporeal shockwaves in a noninvasive manner. The method configured for the treatment of chronic kidney disease (CKD) at any one of CKD stage 1 to CKD stage 4. The method of treatment comprising using non-invasive extracorporeal shockwaves having an energy density of 0.02 to 0.18 mJ/mm2 that are delivered to at least one treatment zone selected from various focal zones encompassing renal structures.

3 Claims, 2 Drawing Sheets

(56) References Cited

U.S. PATENT DOCUMENTS

| | | | |
|---|---|---|---|
| 2007/0016112 A1* | 1/2007 | Schultheiss | A61B 17/22004 601/4 |
| 2007/0142753 A1* | 6/2007 | Warlick | A61N 7/00 601/2 |
| 2007/0239082 A1* | 10/2007 | Schultheiss | A61B 46/17 601/4 |
| 2012/0065552 A1* | 3/2012 | Andrews | A61B 8/08 601/2 |

* cited by examiner

METHOD FOR IMPROVING KIDNEY FUNCTION WITH EXTRACORPOREAL SHOCKWAVES

RELATED APPLICATIONS

This Application is a continuation of U.S. patent application Ser. No. 16/776,901 filed Jan. 30, 2020, presently allowed, which is a continuation of U.S. patent application Ser. No. 15/452,568 filed Mar. 7, 2017, now U.S. Pat. No. 10,583,069, which is in turn a continuation of U.S. patent application Ser. No. 13/359,538 filed Jan. 27, 2012, now abandoned.

FIELD OF THE INVENTION

The present invention relates to a method for treating the kidney with extracorporeal shockwaves in a noninvasive manner and in particular, to such a method for the treatment of the nephrons about the glomerulus.

BACKGROUND OF THE INVENTION

Extracorporeal shockwave therapy (herein referred to as 'ESWT') is non-surgical, non-invasive treatment of medical conditions using acoustic shockwaves. First use of shockwave therapy in the early 1980's was utilized to fragment kidney stones termed shockwave lithotripsy. Continued development of shockwave treatment showed the possibility of stimulating bone formation, angiogenesis, as well as other orthopedic indications. However, medical literature suggests that lithotripsy creates hypertension and some damage to the kidney including hematuria during the procedure.

A shockwave is a form of acoustic energy resulting from phenomena that create a sudden intense change in pressure for example an explosion or lightning. The intense changes in pressure produce strong waves of energy that can travel through any elastic medium such as air, water, human soft tissue, or certain solid substances such as bone.

Shockwaves are characterized by the delivery of a sequence of transient pressure disturbances characterized by an initial high peak pressure with a fast pressure rise followed by rapid wave propagation with diminishing amplitude over its lifecycle. Such that shockwaves characteristically have a quick lifecycle, starting with a big high amplitude pressure peak followed by a gradual diminishing pressure amplitude having amplitude of about 10-20% of the initial pressure peak. Shockwave are further characterized in that they do not produce heat within the tissue.

Shockwaves are therefore characteristically different from ultrasound in that the ultrasound waveform produces constant cyclic sinusoidal amplitude that produces heat at the tissue level. Conversely shockwaves do not have constant amplitude over time.

Acoustic shockwaves are primarily generated by three different methods, electrohydraulic (also referred to as spark gap), electromagnetic (also referred to as 'EMSE'), and piezoelectric. Each method needs an apparatus to focus the generated shockwave so as to provide a focal point and/or focal zone for the treatment area. In the focal zone shockwaves produce much higher pressure impulses as compared with the zones outside of the focal zone.

Mechanical means for focusing each of these methods is generally realized with an appropriate arrangement of surfaces reflecting the wave toward the desired focal point and/or an appropriate arrangement of the generating devices.

Spark gap systems incorporate an electrode (spark plug), to initiate a shockwave, and ellipsoid to focus the shockwave. EMSE systems utilize an electromagnetic coil and an opposing metal membrane. Piezoelectric systems form acoustical waves by mounting piezoelectric crystals to a spherical surface to provide focus. Of the three systems, the spark gap system is generally preferred in the art for generating therapeutic shockwaves ESWT as it introduces more of the generated shockwave energy to the treatment target site.

In spark gap systems, high energy shockwaves are generated when electricity is applied to an electrode positioned in an ellipsoid immersed in treated water. When the electrical charge is fired, a small amount of water is vaporized at the tip of the electrode and a shockwave is produced. The shockwave ricochets from the side of an ellipsoid and converges at a focal point, which may then be transferred to the area to be treated.

In electromagnetic systems an electrical impulse is circulated in a coil. The coil produces an electromagnetic field that expels a metallic membrane to produce the mechanical impulse.

In piezoelectric systems ceramic material with piezoelectric characteristics is subjected to an electrical impulse. The electric impulse modifies the dimension of the ceramic material to generate the desired mechanical impulse. A focal point is attained by covering a concave spherical surface with piezoelectric ceramics converging at the center of the sphere.

The method of focusing the generated shockwave has been greatly described in the art for example in U.S. Pat. Nos. 5,174,280 and 5,058,569, 5,033,456, EP1591070 all of which are incorporated herein by reference as if fully set forth.

Traditionally shockwaves have been used in medicine as a noninvasive means for treating a variety of anomalies such as kidney stones (lithotripsy), fragmentation of calcification, chronic orthopedic inflammation healing, bone healing (osteogenesis), wound healing, revascularization, angiogenesis are well known and described in medical literature.

U.S. Pat. No. 7,507,213 to Schultheiss, et al. discusses invasive stimulation of kidney by surgically exposing the organ for example heart or kidney prior to applying shockwave therapy.

US Patent Publication No. 2011/0257523 to Hastings et al. discusses a method utilizing high intensity focused ultrasound (HIFU) for ablating innervated tissue of the kidney, for denervating renal vasculature, including disruption and termination of renal sympathetic nerve activity, to improve cardiac and/or renal function particularly that associated with hypertension.

SUMMARY OF THE INVENTION

The prior art teaches methods for treating the kidney utilizing high energy shockwave (via lithotripsy utilizing high pressure shockwaves with energy profile of 0.6-1.1 $mJ/mm^2$), or invasive means including necrosis of tissue associated with the kidney, and/or destroying calcification within the kidney.

The present invention overcomes the deficiencies of the background by providing a method for treating kidney and renal structures in a noninvasive, nondestructive manner, without tissue temperature elevation utilizing low pressure shockwaves to treat and/or maintain kidney function and/or improve kidney function and/or conditions associated with the kidney and/or renal structures and/or reduce kidney degradation and/or treat varying stages of chronic kidney disease ('CKD') and/or hypertension.

Within the context of this application the terms aqueous solution, aqueous medium, or aqueous environment may be used interchangeably to refer to an enclosure, opening, lumen, or space that is placed in an aqueous solution or mixture for example including but not limited to water, medicated water, ionized water, oil, gel, treated water or the like solution or mixture in a liquid state.

Within the context of this application the term extracorporeal shockwave therapy ('ESWT') refers to shockwave therapy provided with all forms of shockwave generating device.

Within the context of this application the term shockwave treatment device refers to a device comprising a controller and/or computer and a shockwave treatment applicator as is known in the art. For example, a shockwave treatment device comprises controller and/or computer that controls the shockwave treatment produced by the shockwave treatment applicator.

Within the context of this application the term renal and/or kidney structures refers to any of the following structures nephron, glomerulus, Bowman's capsule, tubules, medulla, renal artery, renal vein, renal pelvis, papilla, adrenal glands, adrenal cortex, adrenal medulla, phrenic arteries, and adrenal vein, neural tissue directly or indirectly innervating the kidney and renal structures, kidney neural system including renal sympathetic and renal para-sympathetic nerves, renal sympathetic nerves that lie within and immediately adjacent to the wall of the renal arteries.

Within the context of this application shockwave properties and/or parameters may be interchangeably represented in different units of measure as is accepted in the art to refer to the same and/or equivalent units of measure. For example shockwave pressure may be interchangeably provided in units of atmospheres ('atm') or Pascals ('pa') or mega Pascals (Mpa). Shockwave frequency may be provided in relative of absolute units, for example including but not limited to hertz ('Hz') and/or shockwaves per unit time, shockwave per minute, or the like.

A preferred embodiment of the present invention provides for a method for noninvasive ESWT of the kidney structures and in particular the glomerulus, for maintaining and/or improving kidney function.

Optionally and preferably the method of treatment according to the present invention may be utilized to improve and/or increase blood flow within the renal and/or kidney structures, for example including but not limited to the nephron and/or glomerulus.

Optionally and preferably the method of treatment according to the present invention may be utilized to remove glomerular calci.

Optionally the method of treatment according to the present invention may be utilized to improve hypertension in a non-destructive manner.

Optionally the method of treatment according to the present invention may be utilized to improve hypertension in an indirect manner for example by improving renal blood flow, renal blood flow within the glomerulus, renal vein and/or artery and/or nerve system, neural tissue directly or indirectly innervating the kidney or renal structures, kidney neural system including renal sympathetic and renal para-sympathetic nerves.

Optionally, the method of treatment of the kidney and more preferably the glomerulus according to the present invention produces a shockwave regimen determined based on at least one or more parameters for example including but not limited to shockwave parameters, treatment protocol parameters, anatomical parameters, or the like.

Optionally protocol parameters for example including but not limited to the number of treatments sessions, the duration of a treatment protocol, timing of active and/or inactive treatment sessions, frequency of session, or the like.

Optionally the number of active treatment sessions may be provided from about 1 session to about 18 sessions. Optionally 12 active treatments may be provided during the treatment protocol according to the present invention. Optionally number of active treatment session may for example be 1, or 2, or 3, or 4 or 5 or 6, or 7 or 8 or 9 or 10 or 11, or 12 or 13 or 14 or 15 or 16 or 17 or 18 or 19 or 20 or so sessions.

Optionally the duration of the treatment protocol according to the present invention may be from about 1 day up to about 18 weeks or the equivalent of 1 day up to about 126 days.

Optionally treatment may be provided periodically, continuously, sequentially, intermittently, according to a schedule comprising consecutive sessions and/or with at least one or more intersession recesses. Optionally the length of the recesses may vary according to the required treatment protocol.

Optionally, shockwave parameters may for example include but are not limited to number of shockwaves, frequency of shockwaves and intensity of the shockwave, or the like.

Optionally shockwave intensity may be provided from about 0.02 mJ/mm$^2$ to about 0.18 mJ/mm$^2$. Optionally and preferably shockwave intensity may be provided from about 0.09 mJ/mm$^2$ to about 0.11 mJ/mm$^2$. Optionally and more preferably shockwave intensity may be provided at about 0.1 mJ/mm$^2$.

Optionally Shockwave pressure utilized in embodiments of the present invention may for example be from about 50 atm to about 200 atm and/or from about 5 Mpa to about 20 Mpa.

Optionally shockwave frequency may be provided from about 60 shockwaves per minute to about 360 shockwaves per minute. Optionally and preferably a shockwave frequency may be provided from about 120 shockwaves per minute to about 240 shockwaves per minute. Optionally and most preferably a shockwave frequency may be provided at about 180 shockwaves per minute.

Optionally shockwave frequency may be provided from about 1 Hz to about 6 Hz. Optionally and preferably a shockwave frequency may be provided at about 2-4 Hz. Optionally and preferably a shockwave frequency may be provided at about 2 Hz.

Optionally the number of shockwaves per treatment session may be provided from about 100 shockwave up to about 5000 shockwaves. Optionally and most preferably about 1800 shockwaves per session may be provided.

Optionally the number of shockwaves per treatment session may be applied to at least one and more preferably a plurality of treatment zones optionally and preferably defined by kidney structures. Optionally and more preferably a plurality of zones from about 5 up to about 15 zones may be treated during a treatment session. Optionally the number of shockwaves may be distributed about a plurality of treatment zones in any manner required for the treatment, for example including evenly distributing the number of shockwaves based on the number of zones, or by unevenly distributing the number of shockwaves per zones. For example, a plurality of zones from about 5 to about 15 zones may be treated with 100 shockwaves to about 500 shockwaves within a treatment session to provide for a treatment protocol including about 1800 shockwaves to renal structures, about a plurality of zones.

Optionally the shockwave treatment according to the present invention may be applied to kidney structures from at least one or more optional approaches for example including but not limited to prone, lateral, supine, or any combination thereof, providing for appropriate non-invasive access to the kidney structures to be treated.

A preferred embodiment of the present invention provides a method for improving renal function by applying a non-invasive, nondestructive, extracorporeal shockwave treatment protocol to at least one kidney structure, wherein the shockwave parameters define a low energy shockwave having a frequency of about 2 Hz and energy density of about 0.02 to 0.18 mJ/mm$^2$.

Optionally the treatment according to the present invention may be applied to a renal structure selected from the group consisting of nephron, glomerulus, Bowman's capsule, tubules, medulla, renal artery, renal vein, renal pelvis, papilla, adrenal glands, adrenal cortex, adrenal medulla, phrenic arteries, and adrenal vein, neural tissue directly or indirectly innervating the kidney and renal structures, kidney neural system including renal sympathetic and renal para-sympathetic nerves, renal sympathetic nerves that lie within and immediately adjacent to the wall of the renal arteries.

Optionally the treatment may be directed at the glomerulus.

Optionally the treatment may be directed or otherwise adapted for applying treatment to the renal artery.

Optionally the shockwave treatment may be dispersed about a plurality of treatment zones, about the kidney structures. Optionally kidney structures may for example include but is not limited to from about 5 treatment zones and up to about 15 treatment zones.

Optionally the shockwave treatment may be applied to a subject from at least one or more approaches and/or positions for example including but not limited to lateral, prone and supine, or any combination thereof.

Optionally the treatment may be provided to provide at least one or more selected from at least one or more of the following reduce renal infiltration by macrophages, renal infiltration by lymphocytes, decreased expression of MCP 1 and decreased expression of CD3 mRNA, reduced Resistive Index, restored blood flow velocity in interlobular renal arteries.

Optionally a total of 2400 shockwave are delivered to at least one or more of the kidney structures, with a treatment energy density of about 0.02 to about 0.18 mJ/mm$^2$; at a frequency of about 2 Hz. Optionally the treatment may be dispersed about a plurality of treatment zones and each treatment zone may be provided with at least 100 shockwaves.

Optionally the treatment according to optional embodiments of the present invention provides for at least one or more selected from the group consisting of: inducing regulatory factors selected from the group consisting of: vascular endothelial growth factor (VEGF), fibroblast growth factors (FGF), angiopoietins (Ang), platelet-derived growth factor, angiogenin, angiotropin, hepatocyte growth factor, platelet endothelial cell adhesion molecule, angiostatin, endostatin, thrombospondin, CXC chemokines, Nitric oxide synthesis, NFkapaB activation, TNF-alpha mRNA expression, increase blood flow in treatment area, decreases the expression of MCP 1, decrease expression of CD3 mRNA, and pigment epithelium, the like or any combination thereof.

Optionally the method according to an optional embodiment of the present invention provides for the treatment of any one or more selected from the group comprising: renal dysfunction, chronic kidney disease (CKD) at any stage (1-4), Renal Insufficiency, proteinuria, diabetic nephropathy on glomerulus, vascular lesions, glomerulus calcification, tubulo-interstitial lesions, reduced blood flow in the interlobular renal arteries, renal artery stenosis any combination thereof.

Optionally the method may provide for the reduction of the blood pressure of the patient.

Optionally the method may provide for the reduction of intra-glomerular hypertension.

Optionally the method may be provided for maintaining kidney function and/or improving kidney function and/or reduce kidney degradation, any combination thereof or the like.

Optionally the method may be provided for treating chronic kidney disease (CKD) at any stage, and/or hypertension.

Optionally the method may be provided for improving conditions associated with the kidney, renal structures.

Optionally the method may be provided to affect neural function or neural activity associated with the kidney structures.

Optionally wherein the affects are selected from the group consisting of: regenerating neural tissue, normalization of neural function, normalization of neural activity, modification of neural function, modification of neural activity, regulating neural activity, regulating neural function, inhibiting neural activity, inhibiting neural function, promoting neural activity, promoting neural function, any combination thereof.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The principles and operation of the present invention may be better understood with reference to the drawings and the accompanying description.

Figure 1:
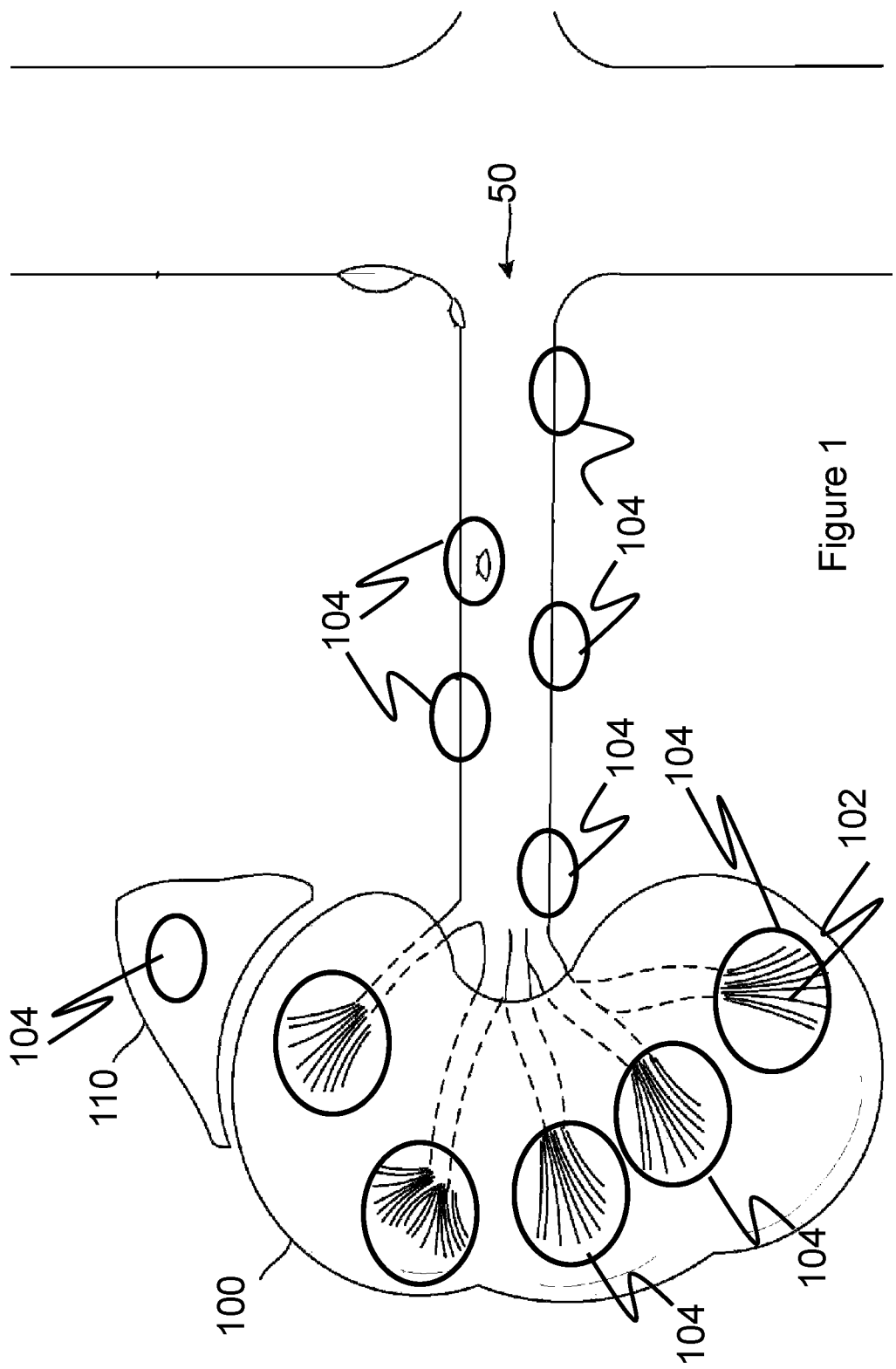
FIG. 1 is a schematic illustrative diagram of the kidney showing the kidney structures including the adrenal gland; and optional treatment zones comprising the nervous system innervating the kidney and the renal artery.

FIG. 1 provides an illustrative schematic diagram of the kidney structures including kidney 100, adrenal gland 110, nephron and glomerulus 102, and renal artery 50. FIG. 1 further provides a schematic illustration of a plurality of optional focal zones and/or treatment zones 104 depicted about the kidney 100 and kidney structures associated with the kidney.

A preferred embodiment of the present invention provides for applying non-destructive and non-invasive ESWT to such kidney structures and in particular to glomerulus 102, adrenal gland, 110 and renal artery 50, and the neural tissue associated with and/or innervating the kidney structures. Most preferably the non-invasive ESWT applied improves overall kidney function. Optionally and preferably the ESWT treatment is provided to treat and/or maintain kidney function at its current level therein reducing kidney degradation due to chronic diseases such as hypertension, diabetes, and/or reduced kidney function. Optionally and preferably the ESWT of the kidney according to the present invention further leads to an overall improvement in kidney function and/or conditions associated with the kidney and/or renal structures.

Optionally the ESWT treatment according to the present invention may be provided to treat chronic kidney disease ('CKD') at any stage.

Optionally the ESWT treatment according to the present invention may be provided to treat hypertension.

Most preferably the applied shockwaves are provided in a noninvasive, nondestructive manner, and do not cause tissue temperature elevation while utilizing low pressure amplitude, low energy shockwaves to bring about the treatment to the kidney structures.

Most preferably the ESWT according to the present invention is provided under the visual guidance of an imaging device for example including but not limited to an ultrasound, CT, MRI or the like imaging technology and/or devices as is known and practiced in the art.

Most preferably imaging device and/or technology provides for aiding in defining the ESWT focal zone where treatment is to be applied for example including but not limited to the glomerulus 102, and/or adrenal gland 110, renal artery 50.

Optionally and preferably the shockwave treatment protocol may be focused on the glomerulus to bring about improved blood flow therethrough and associated kidney structures. Optionally the treatment according to the present invention may optionally further provide for removing glomerular calci.

Optionally the ESWT treatment protocol according to the present invention may provide for the treatment of neural tissue and/or neural function of tissue associated with the kidney and kidney structures via optional pathways for example including but not limited to regenerating neural tissue and/or normalization of neural function and/or normalization of neural activity and/or modification of neural function and/or modification of neural activity and/or regulating neural activity and/or regulating neural functions and/or inhibiting neural activity and/or inhibiting neural function and/or promoting neural activity and/or promoting neural function, the like, or any combination thereof.

Optionally and preferably ESWT treatment according to the present invention provides for a cascade of molecular activity that brings about improved renal blood flow through the glomerulus and/or other renal structures and/or restored blood flow velocity in interlobular renal arteries.

Optionally a cascade of molecular activity may for example, involve but is not limited to at least one or more of the following regulatory factors selected from the group consisting of: vascular endothelial growth factor (VEGF), fibroblast growth factors (FGF), angiopoietins (Ang), platelet-derived growth factor, angiogenin, angiotropin, hepatocyte growth factor, platelet endothelial cell adhesion molecule, angiostatin, endostatin, thrombospondin, CXC chemokines, Nitric oxide synthesis, NFkapaB activation, TNF-alpha mRNA expression, decreases the expression of MCP1, decrease expression of CD3 mRNA, and pigment epithelium.

Optionally the shockwave parameters utilized may be: a frequency of about 2 Hz and energy density from about 0.02 to about 0.18 mJ/mm$^2$.

Most preferably the shockwave parameters utilized are energy density of about 0.09 to about 0.1 mJ/mm$^2$; at a frequency of about 2 Hz.

Optionally each treatment session may comprise up to about 5000 shockwaves. Most preferably each treatment comprises about 2400 shockwave that are delivered to the kidney structure. Optionally the number of shockwaves per treatment session may be applied to at least one and more preferably a plurality of treatment zones 104 about the kidney structures. Optionally and more preferably a plurality of zones from about 5 up to about 15 zones may be treated during a treatment session. Optionally each zone may be treated with about 100 shockwaves to about 500 shockwaves, that may distributed amongst a plurality of zones from about 5 zones to about 15 zones forming the kidney structures.

Optionally treatment may be provided at a particular structure or about a plurality of structures within one treatment session.

Optionally treatment may be provided from different approaches to the kidney structures.

Figure 2:
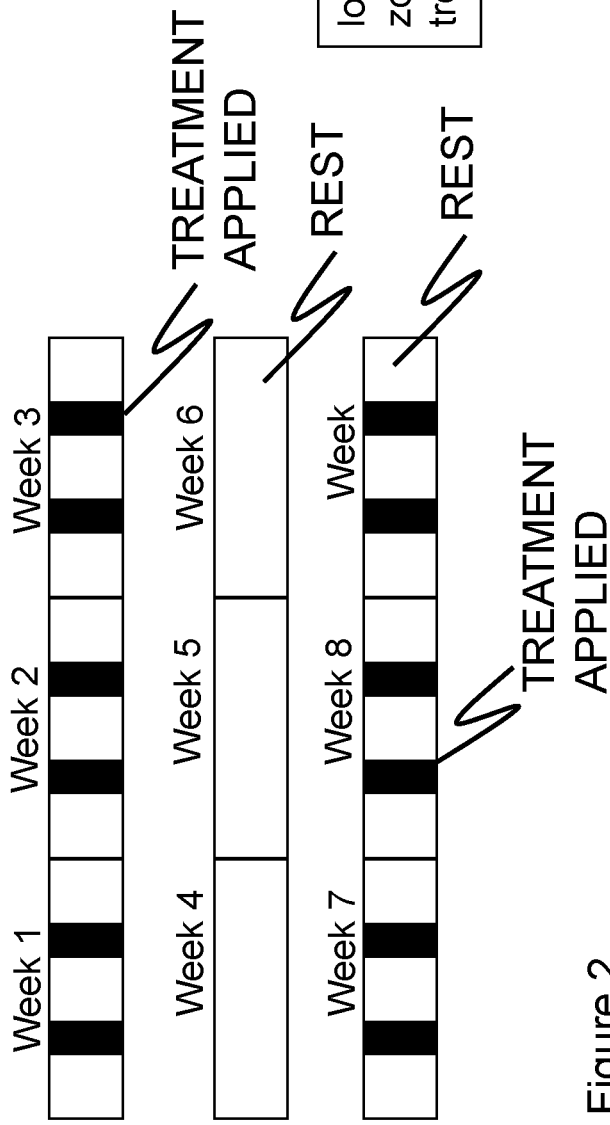
FIG. 2 is a schematic illustrative diagram of a Gantt chart of an optional treatment protocol according to the present invention.

FIG. 2 shows a schematic non-limiting treatment protocol according to the present invention where non-invasive ESWT treatment is provided to a kidney structure where treatment is provided over a span of 9 weeks, as shown. The optional treatment protocol calls for 2 active treatment sessions per week during weeks 1, 2, 3, 7, 8, and 9, while no treatment is provided during weeks 4-6.

Figure 3:
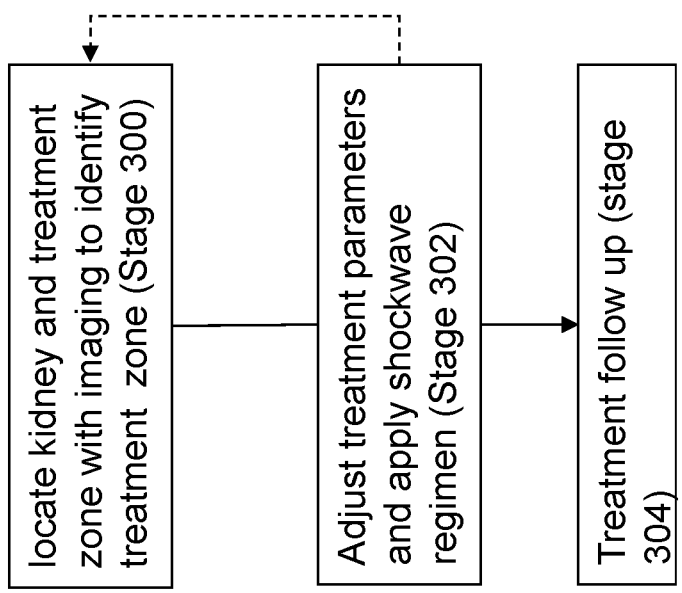
FIG. 3 is a flowchart of an exemplary method according to the present invention for ESWT of kidney structures.

FIG. 3 shows a flowchart of an optional method of treatment of the kidney structures according to an optional embodiment of the present invention. First in stage 300 the kidney structure to be treated is located with an imaging device, for example including but not limited to ultrasound. Optionally and preferably the kidney structure to be treated is identified from the prone approach. Next in stage 302, the shockwave regimen is selected, treatment protocol adjusted and applied. Most preferably treatment protocol comprises 1800 shockwaves with shockwave frequency of 2 Hz, and energy density of about 0.1 mJ/mm$^2$. Optionally either one or both kidneys are treated; optionally each kidney may be treated in turn, with shockwave regimen including 900 shockwaves with shockwave frequency of 2 Hz, and energy density of about 0.1 mJ/mm².

Optionally treatment of 2400 shockwaves is distributed amongst various kidney structures forming a plurality of treatment zones, for example from about 5 zones up to about 15 zones, therein providing from about 100 to about 500 shockwaves per treatment zones.

Optionally the shock treatment may be applied to kidney structures from a plurality of optional approaches for example including but not limited to prone (back), lateral (side), supine (stomach) any combination thereof providing for appropriate non-invasive access to the kidney structures to be treated. For example, an optional treatment protocol may call for 900 shockwaves to be provided from the lateral position and 900 from the prone position.

For example, an optional treatment protocol may for example call for 1800 shockwaves delivered at a frequency of 2 Hz, with energy density of about 0.1 mJ/mm². Optionally the 2400 shockwaves may be distributed about both kidneys amongst a plurality of treatment zones, from a plurality of zones for example:

100 shockwaves from the prone position targeting a kidney structure forming a single treatment zone of the left kidney, with frequency of 3 Hz with energy density of 0.06 mJ/mm²;

Next the right kidney is treated with 1650 shockwaves with frequency of 2 Hz with energy density of 0.1 mJ/mm² distributed about a plurality of treatment zones and kidney structures from a plurality of approaches (position) as follows;

100 shockwaves from the prone position targeting a first kidney structure forming a first treatment zone of the right kidney;

next 650 shockwaves from the lateral position dispersed about a plurality of treatment zones comprising a second treatment zone provided with 300 shockwaves, a third zones provided with about 100 shockwaves and a fourth treatment zone provided with about 250 shockwaves;

next a further 900 shockwaves from the prone position delivered to a plurality of treatment zones, a fifth zone provided with 300 shockwaves and finally a sixth zone provides with 600 shockwaves.

Optionally and preferably treatment is repeated as necessary about at least one or more focal zones 104.

Lastly, in stage 304 following treatment of all renal structures and/or zones a follow up period applied based on the structure treated.

While the invention has been described with respect to a limited number of embodiments, it will be appreciated that many variations, modifications and other applications of the invention may be made.

What is claimed is:

1. A non-invasive method for treating chronic kidney disease (CKD) at any stage selected from CKD stage 1 to CKD stage 4, the method provided in the form of non-invasive focused extracorporeal shockwave therapy ('ESWT'), the method comprising applying between 1 and 2400 focused shockwaves having a repetition rate above one shockwave per second, and energy density of about 0.02 to 0.18 millijoule per millimeter squared (mJ/mm2), applied to at least one treatment zone comprising: nephron, glomerulus, Bowman's capsule, tubules, medulla, renal artery, renal vein, renal pelvis, papilla, adrenal glands, adrenal cortex, adrenal medulla, phrenic arteries, and adrenal vein, neural tissue directly or indirectly innervating a kidney and renal structures, kidney neural system including renal sympathetic and renal para-sympathetic nerves, and renal sympathetic nerves that lie within and immediately adjacent a wall of a renal artery, or any combination thereof;

using an imaging device to aid in defining the at least one treatment zone, wherein the at least one treatment zone is provided with at least 100 shockwaves; and, wherein the shockwaves are delivered to the at least one treatment zones during at least one session per week for up to about 20 sessions within a time frame of up to about 18 weeks.

2. The method of claim 1, wherein the at least one treatment zone comprises 5 treatment zones to 15 treatment zones.

3. The method of claim 1, wherein the at least one treatment zone is the glomerulus so as to bring about a reduction of intra-glomerular hypertension.

\* \* \* \* \*